(12) United States Patent
Køhnke (10) Patent No.: US 6,578,574 B1
(45) Date of Patent: Jun. 17, 2003

(54) DEVICE FOR ADMINISTERING ARTIFICIAL RESPIRATION TO A PATIENT

(75) Inventor: Ole B. Køhnke, Glostrup (DK)

(73) Assignee: Ambu International A/S, Glostrup (DK)

( * ) Notice: Subject to any disclaimer, the term of this patent is extended or adjusted under 35 U.S.C. 154(b) by 0 days.

(21) Appl. No.: 09/647,240
(22) PCT Filed: Mar. 26, 1999
(86) PCT No.: PCT/DK99/00176
§ 371 (c)(1), (2), (4) Date: Jan. 19, 2001
(87) PCT Pub. No.: WO99/49924
PCT Pub. Date: Oct. 7, 1999

(30) Foreign Application Priority Data

Mar. 31, 1998 (DK) .............................................. 0449/98

(51) Int. Cl.[7] ............................................. A61M 16/00
(52) U.S. Cl. .............................. 128/203.11; 128/204.28; 128/205.14
(58) Field of Search ....................... 128/202.28, 202.29, 128/203.11, 204.28, 205.13, 205.14, 205.15, 205.16, 203.28

(56) References Cited

U.S. PATENT DOCUMENTS

| 3,158,152 A | * | 11/1964 | Bloom | ................... 128/202.29 |
|---|---|---|---|---|
| 4,764,346 A | * | 8/1988 | Lewis et al. | ........... 128/204.28 |
| 4,782,831 A | | 11/1988 | Gallant | |
| 4,821,712 A | | 4/1989 | Gossett | |
| 5,305,739 A | * | 4/1994 | Gray | ..................... 128/205.13 |
| 5,427,091 A | | 6/1995 | Phillips | |
| 5,558,371 A | * | 9/1996 | Lordo | .................... 128/205.13 |
| 5,628,305 A | | 5/1997 | Melker | |

* cited by examiner

Primary Examiner—Weilun Lo
Assistant Examiner—Mital Patel
(74) Attorney, Agent, or Firm—Dykema Gossett PLLC (57) ABSTRACT

The invention relates to a device for performing artificial respiration on a patient, comprising a container (1) which defines an inner volume relative to the ambient and has a first opening accommodating a valve arrangement (2, 14) which allows inflow of air or gases from the outer area to the inner area, and a second opening in connection with which there is provided a valve arrangement (3, 16) which allows outflow from the container and prevents inflow to the container through the second opening. An expansible means (7) is provided in the container and adapted to expand upon action from the outer area to displace air and/or other gases in the container (1) out through the second opening. This improves the certainty that oxygen and/or other gas finds its way to the patient's air passages.

9 Claims, 7 Drawing Sheets

DEVICE FOR ADMINISTERING ARTIFICIAL RESPIRATION TO A PATIENT

BACKGROUND OF THE INVENTION

1. Field of the Invention

The invention relates to a device for performing artificial respiration on a patient.

2. The Prior Art

Devices of this type are known as resuscitators. These are used within the medical field when a patient is unable to breath correctly, or when the patient does not breath at all, e.g., because of deep unconsciousness. Such devices are used not only at hospitals, but also in many other connections where first aid equipment finds application.

Such a device comprises a container which defines an inner volume with respect to the ambient, and which is provided with a first opening accommodating a valve arrangement which allows inflow of air and/or other gases from the outer area to the inner area, a second opening in connection with which there is provided a valve arrangement which allows outflow from the container and prevents inflow to the container through the second opening, and a mouthpiece adapted to be fitted over the openings of a patient's air passages for the delivery of the air and/or gas flowing out of the container to the patient. Using a known device, the mouthpiece is held against the patient's face by one hand, while the container is squeezed by the other hand to force the air or gas present in the container out of the container.

However, it has been found that such devices for performing artificial respiration on a patient, where such devices are in the hands of persons having no or only little practice, does not provide satisfactory breathing assistance. The reason is that it may be difficult to hold the mouthpiece correctly relative to the patient's face by one hand to ensure that the area around the air passages is sealed completely, so that no air flows out along the edge of the mouthpiece, while squeezing the container by the other hand to press the air and/or gas present in the container into the patient. Part of the air or gas pressed out is thus lost to the ambient. Clearly, this may have serious consequences for the patient's health.

The object of the present invention is to provide a device of the type mentioned in the foregoing, by means of which it may be ensured with greater certainty, also when unpractised persons use the device, that the patient receives the maximum intended amount of the air pressed out of the container.

SUMMARY OF THE INVENTION

This is achieved according to the invention in that an expansible means is provided in the container and adapted to expand upon action on the outer area to displace air or other gases in the container out through the second opening.

When such an expansible means is arranged in the container, it is no longer necessary to squeeze the container by one hand to force the air present in it out through the second opening and into the patient. It is thus possible to use both hands for holding the mouthpiece relative to the patient's face, while expansion of the expansible means displaces the air from the interior of the container and into patient, and it is thus ensured that air does not, or only to a limited extent, get past the edges of the mouthpiece. The intended amount of air is thus delivered to the patient.

In an expedient embodiment, the container may be compressible, as the wall of the container is elastic and flexible, so that, if desired, the device may also be used under more controlled conditions, e.g. at a hospital where experienced staff is present to hold the mask of the device in engagement with the patient's face. After manual compression of the container, air or oxygen is conventionally sucked into the inner volume because of the elasticity of the wall.

In an expedient embodiment, the expansible means is thus formed by an inflatable means. The means involved may be a means which is inflatable by means of the assistant's expiration air. The interior of the expansible means is hereby isolated from the interior of the container, and there is thus no risk of contagious diseases being transmitted via this device.

The container used may be of the known compressible type or may be a rigid or relatively rigid container. In connection with the invention it is exclusively required that the container used can present a counterpressure on the expansion of the expansible element, and that the container is essentially dimensionally stable when air or gas is sucked in from the ambient.

Particularly expediently, the expansible means is a self-contractible means. Hereby the self-contractible means will suck in air through the first opening during its self-contracting function. The self-contracting force of the expansible means must be sufficient to open the valve arranged at the first opening.

In this connection the expansible means may be formed by a bag of a flexible sheet material and an elastic material, e.g. an elastic net, arranged on the outer side of this sheet material, a balloon of an elastic rubber material or a bag of a flexible sheet material formed with corrugations or folds which, when relieved, contract the bag.

The expansible means preferably comprises a connecting element adapted to cooperate with a complementary connecting element arranged in an opening in the container. The opening in the container for the connecting element of the expansible means is preferably arranged such that the assistant, when performing the artificial respiration, can get access to the mouthpiece with his mouth.

The invention moreover relates to a container for use in connection with a resuscitator described in the foregoing. Such a container comprises an opening through which a gas can flow into the container, an opening through which a gas can flow out of the container, and an opening through which an expansible means may be inserted into the container. If this container is used in connection with a normal resuscitator which operates by compression by hand, this opening for the insertion of an expansible means may be closed by a cap. In this connection the container must satisfy the above-mentioned criteria for such a container.

The invention moreover relates to an expansible means for use in a resuscitator as described in the foregoing. Such an expansible means comprises a mouthpiece for the injection of air. The expansible means is expediently shaped as described in the foregoing, viz. either as a bag of a flexible sheet material and an elastic material, e.g. an elastic net, arranged on the outer side of it, a balloon of an elastic rubber material or a bag of a flexible material formed with corrugations or folds which, when relieved, contract the bag.

The invention will be explained more fully below with reference to the drawing, in which

BRIEF DESCRIPTION OF THE DRAWINGS

The invention will be explained more fully below with reference to the drawing, in which.

DETAILED DESCRIPTION OF THE PREFERRED EMBODIMENT

Figure 1:
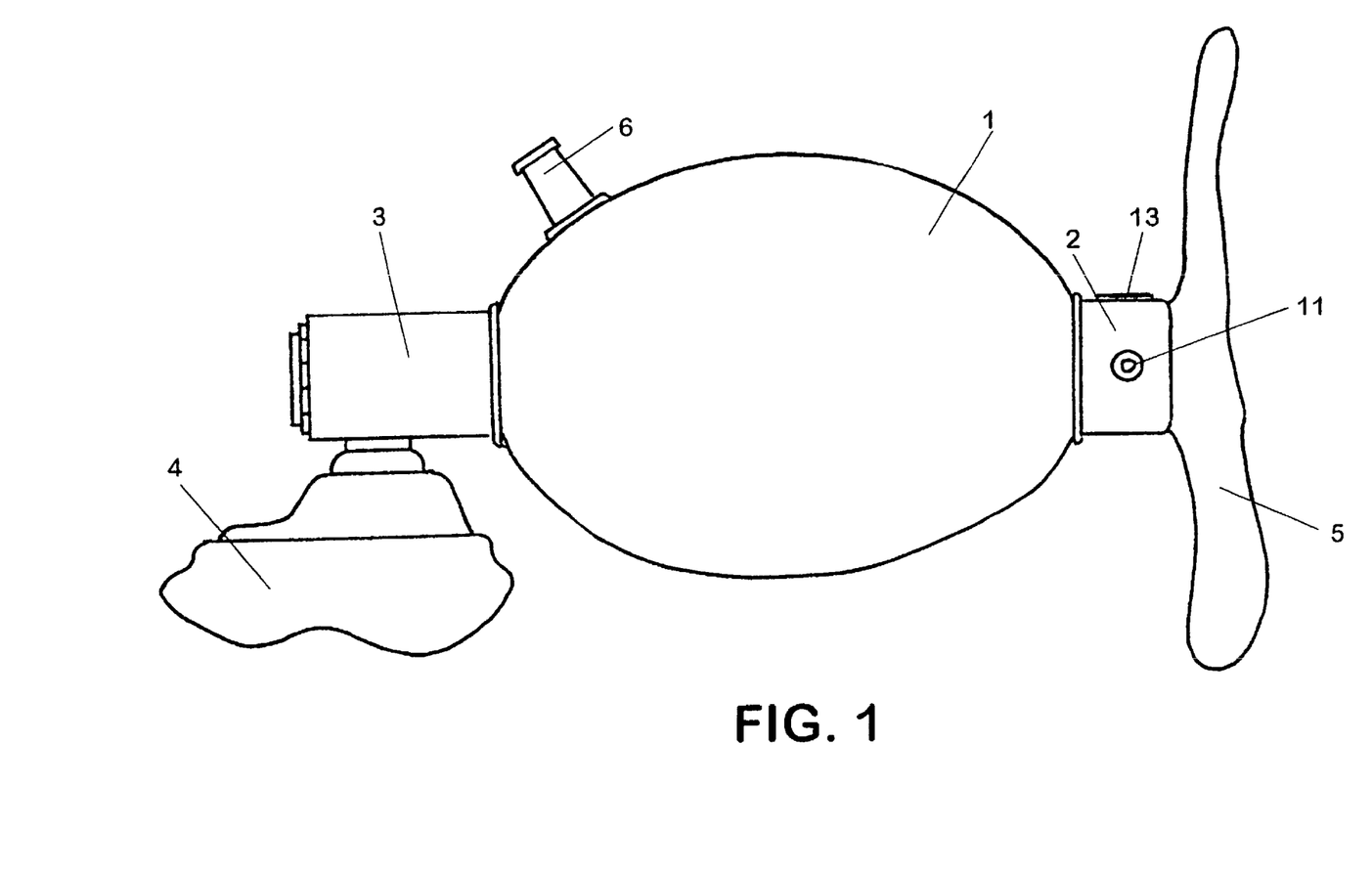
FIG. 1 shows a device according to the invention, seen from the side.

It appears from FIG. 1 that the resuscitator comprises a container 1, an inlet valve housing 2 arranged in connection with a first opening in the container 1, and a patient valve housing 3 arranged in connection with a second opening in the container 1. A reservoir bag 5 is mounted in connection with the inlet valve housing 2. The inlet valve housing 2 comprises an inlet channel 11 for oxygen or a similar gas. A pressure relief valve 13 is provided on the upper side of the inlet valve housing. A mouthpiece 4 is provided in connection with the patient valve housing 3. The mouthpiece comprises a flexible edge area which can conform to the shape of the patient's face upon application of pressure. Further, an expansible body is mounted in the container 1, with a mouthpiece 5 associated with this protruding through an opening in the container 1.

It appears from FIG. 1 that the resuscitator comprises a container 1, an inlet valve housing 2 arranged in connection with a first opening in the container 1, and a patient valve housing 3 arranged in connection with a second opening in the container 1. A reservoir bag 5 is mounted in connection with the inlet valve housing 2. The inlet valve housing 2 comprises an inlet channel 11 for oxygen or a similar gas. A pressure relief valve 13 is provided on the upper side of the inlet valve housing. A mouthpiece 4 is provided in connection with the patient valve housing 3. The mouthpiece comprises a flexible edge area which can conform to the shape of the patient's face upon application of pressure. Further an expansible body is mounted in the container 1, with a mouthpiece 6 associated with this protruding through an opening in the container 1.

Figure 2:
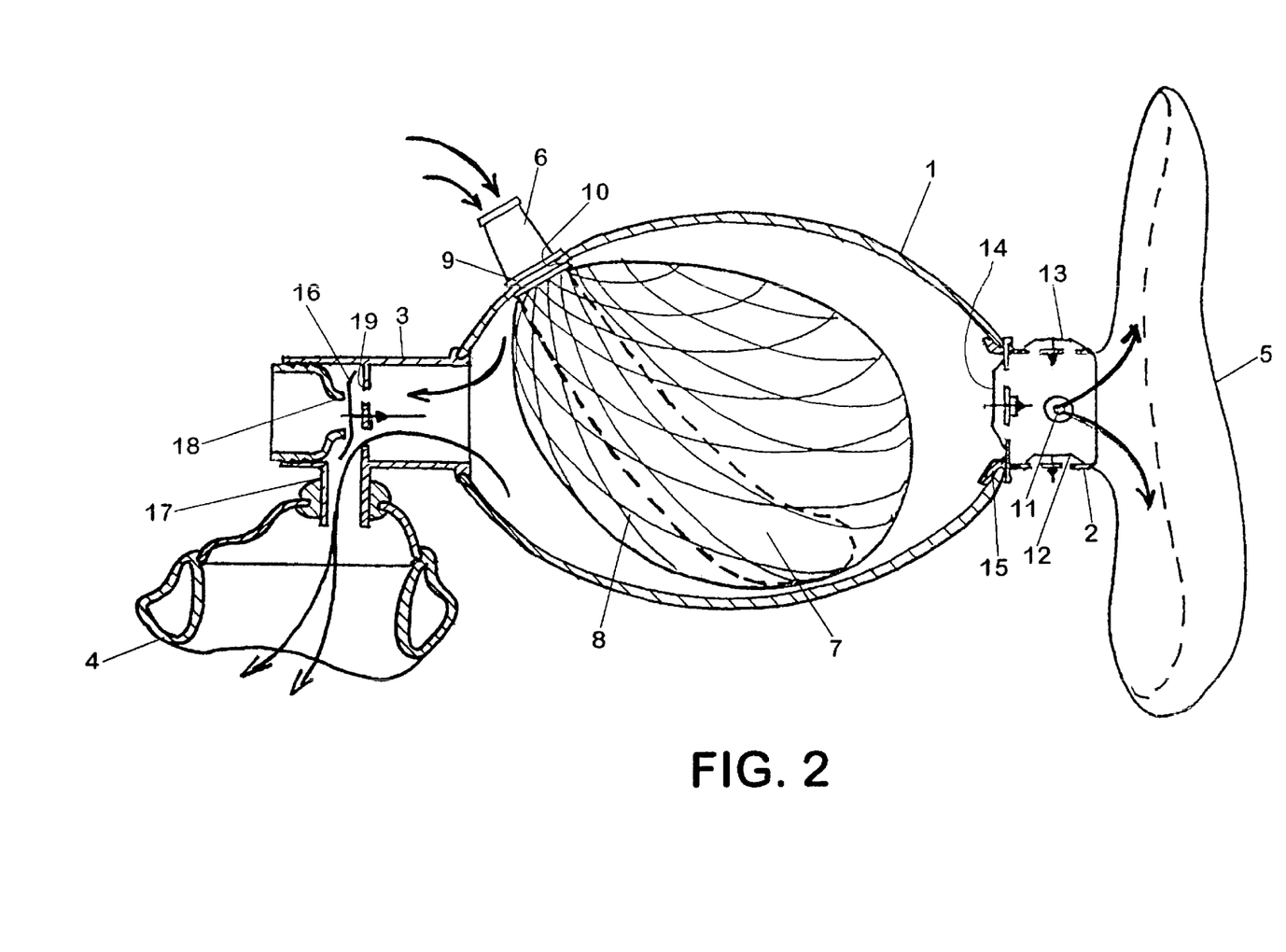
FIG. 2 shows the device of FIG. 1 in section during the expansion of the expansible means.

FIG. 2 shows a sectional view in a situation where air is injected into the expansible means through the mouthpiece 6. In this connection, the flow through the various valve arrangements is shown by arrows. The expansible means comprises a flexible sheet material 7 and a net of an elastic material 8. Upon expansion of the expansible means, the elastic net 8 will offer limited resistance to the expansion. As the expansible means is expanded, the valve body 14 in the inlet valve housing 2 will shut off flow out through the first opening in the container because of the pressure increase in the interior of the container. At the same time, oxygen and/or another gas flows in through the channel 11 and fills the reservoir bag 5. When the bag 5 is filled completely, any additional inflow of oxygen will force the valve 13 to an open position and such oxygen will thus escape through this opening. If oxygen or the like is not admitted through the channel 11, ambient air can be sucked in through the valve arrangement 12. It moreover appears from the figure that the inlet valve housing 2 is connected with the container 1 by an annular flange 15 on the inlet valve housing 2. The expansion of the expansible means will cause the air or gas present in the container 1 to be forced out through the second opening and hereby cause the valve body 16 to assume a position in which it permits flow out through openings in a wall 19 in the patient valve housing 3 and further through a branch 17 to the mouthpiece 4 and from there further inwards through the patient's air passages. In this situation the valve body 16 shuts off the ambient, as the valve body engages the edge of the opening 18 toward the ambient. It moreover appears that the mouthpiece 6 associated with the expansible means is mounted in the container 1 by a groove 9 which cooperates with the edge of an opening 10 in the container.

Figure 3:
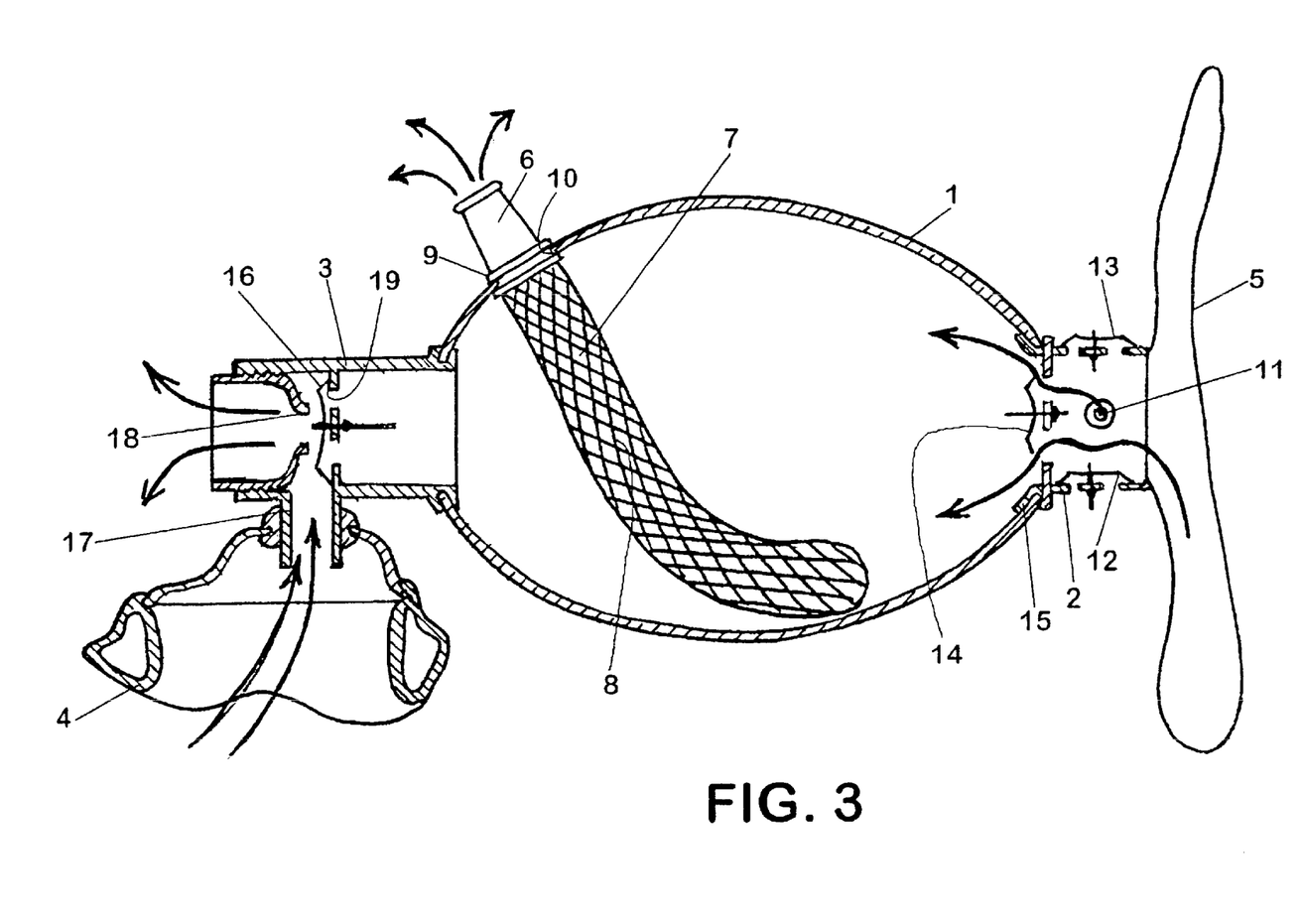
FIG. 3 shows the device of FIG. 1 in section during the contraction of the expansible means.

FIG. 3 shows a situation where the expansible means is being contracted. In this situation, the valve body 14 will open because of the self-contractible effect of the expansible means provided by the elastic net 8, and the air or the oxygen present in the reservoir bag 5 will be sucked in through the opening at the valve body 14. The gas simultaneously flowing in through the channel 11 will be sucked into the interior of the container 1 together with the gas already present in the reservoir bag. In this situation, both the pressure relief valve 13 and the suction valve 12 are closed. If no gas were introduced into the reservoir bag through the channel 11, ambient air would in this situation be sucked in through the opening at the valve body 12 and through the opening at the valve body 14 and into the interior of the container. It moreover appears that in this situation the valve body 16 engages the wall 19 and shuts off access from the ambient to the interior of the container via the second opening. At the same time, the patient's expiration air will flow past the valve body and toward the ambient through the opening 18.

Figure 4:
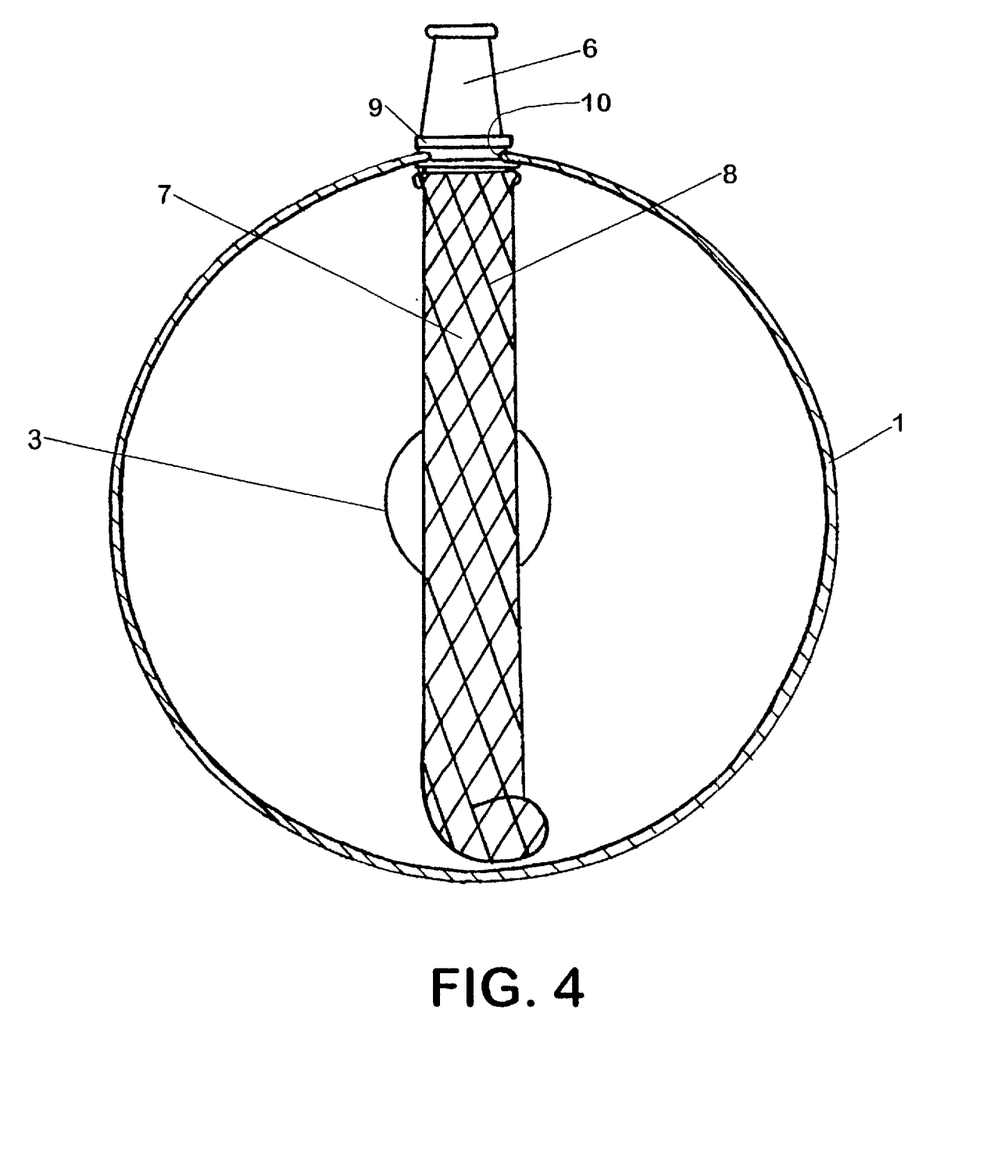
FIG. 4 shows the device of FIG. 1 in section along the line 4—4.

FIG. 4 is a sectional view of the device shown in FIG. 1, where the expansible means is mounted in an opening in the wall of the container 1. The patient valve housing 3 at the second opening is moreover visible behind the expansible means.

Figure 5:
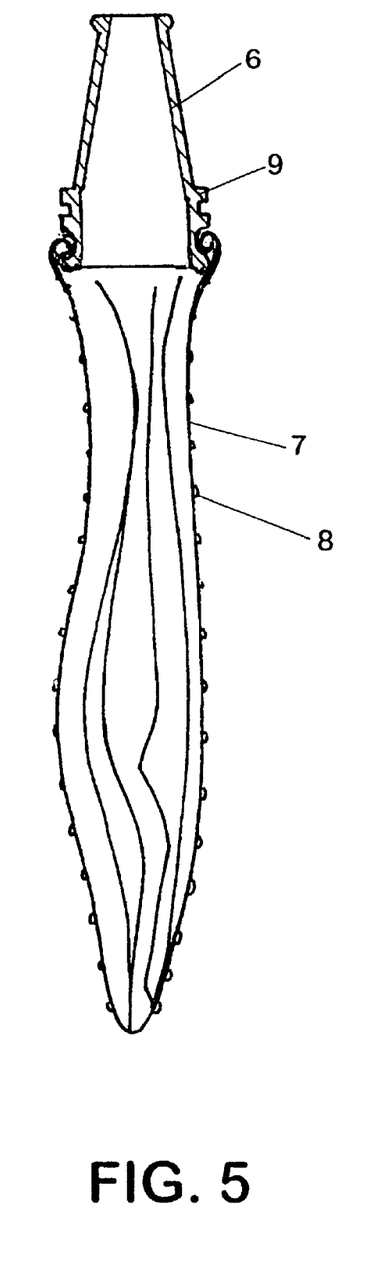
FIG. 5 shows an expansible means, as shown in FIGS. 2, 3 and 4 in section.

FIG. 5 is a sectional view of an expansible means as shown in FIGS. 2–4. The elastic net 8 is mounted externally on the flexible sheet bag 7. Two annular flanges 9 define a groove between them for receiving the edge of an opening in the container wall. It should be mentioned in this connection that other connections are possible between the expansible means and the container. Thus, a connecting element may be provided in the container where it may cooperate with a complementary connecting element on the expansible means, e.g. on the mouthpiece of the expansible means. A bayonet socket, a threaded connection, a conical frictional connection, a press fit or the like may be involved in this connection.

Figure 6:
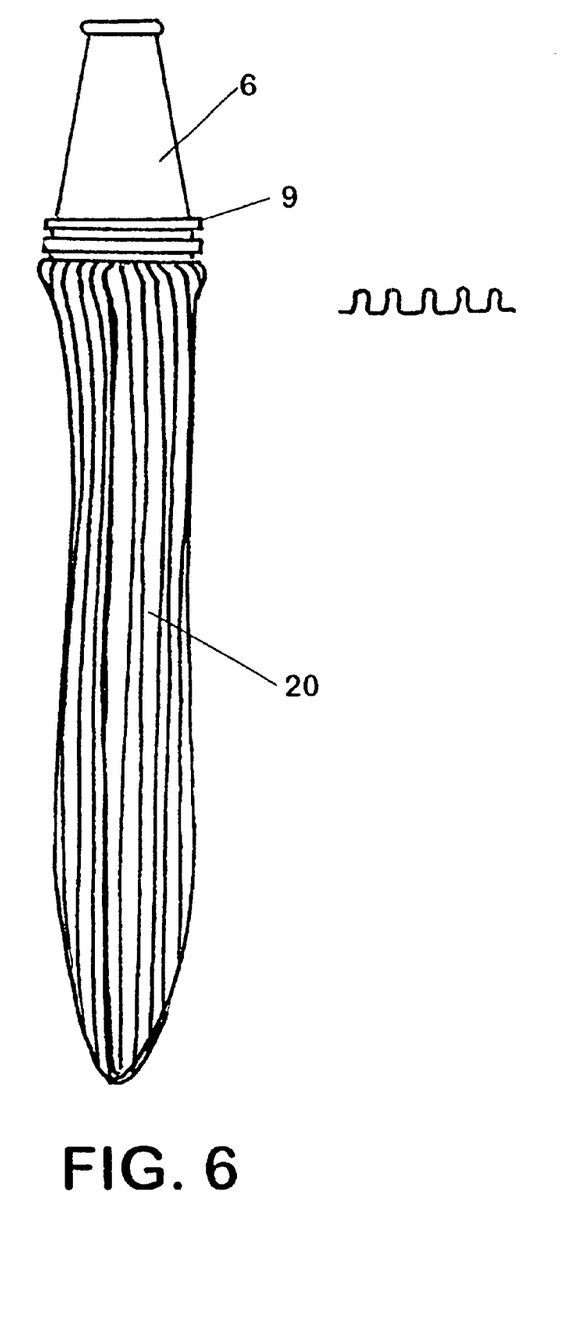
FIG. 6 shows a first alternative embodiment of an expansible means.

FIG. 6 shows an alternative embodiment of an expansible means for use in a device as shown in FIGS. 1 to 3. The device shown here comprises a corrugated or folded bag which, following expansion and upon relief, will contract the bag, as the folds give rise to an application of force.

Figure 7:
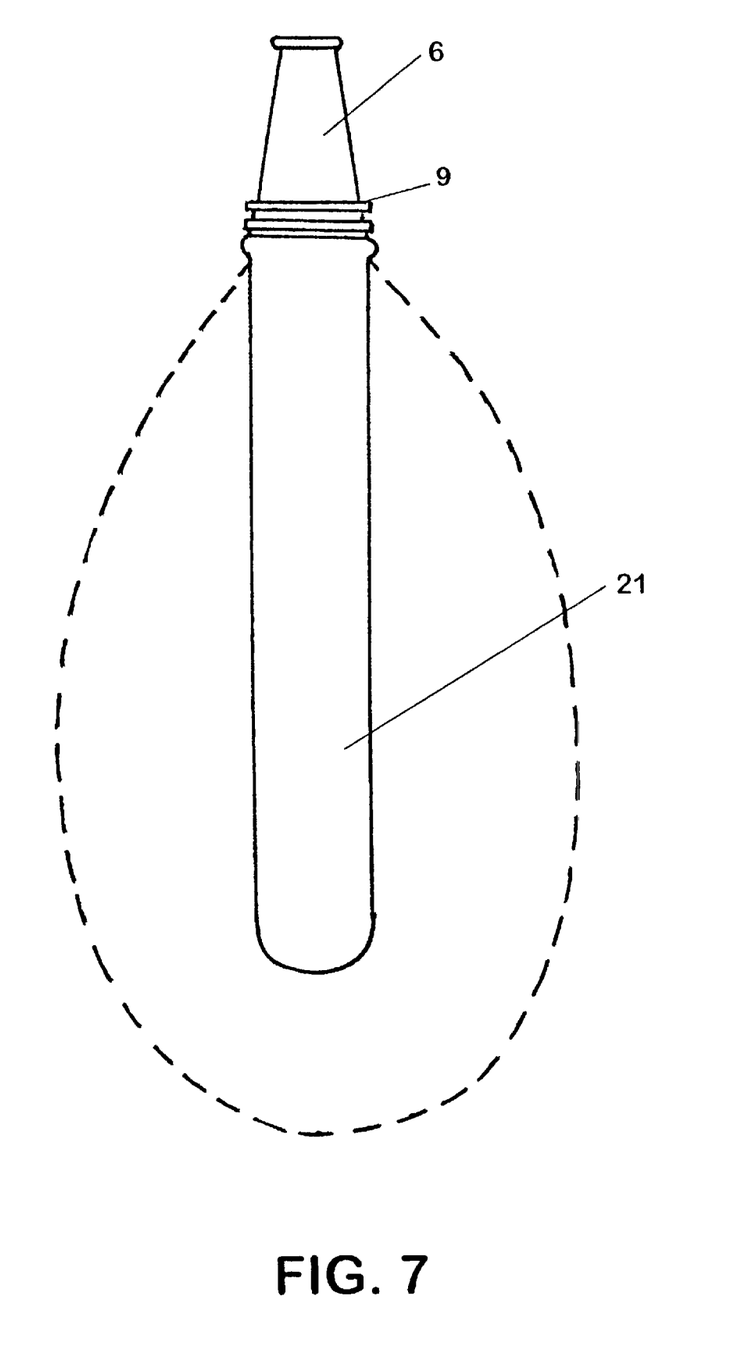
FIG. 7 shows a second alternative embodiment of an expansible means.

FIG. 7 shows a further alternative embodiment of the expansible means. A balloon of an elastic material is involved here. An expanded form of the balloon is shown in dashed line.

In the embodiment described, the expansible means may be produced at low cost in terms of consumption of material and on automatic machinery and permits an expedient adaptation of the functional properties.

The means may be made of tubular flexible sheet, e.g. polyethylene, which is pulled inwardly over a rigid plate that forms a support for the sheet. Highly elastic thin rubber thread, preferably surrounded by fabric, is then wound helically around the supported sheet tube with a suitable pitch and with suitable stretching of the thread. The ends of the thread are secured by gluing to the sheet at both ends, and longitudinal sheet strips, likewise of polyethylene sheet, are spot welded on both sides of each thread cross.

A suitable number of straps for the thread is formed hereby, maintaining the helical position, without preventing the thread from sliding through these straps. The sheet tube is then welded and retained at the edges at the other end of the support plate before this is pulled out, and transverse welding is performed to seal the bag.

The bag is then released, whereby the bias of the elastic thread will fold the sheet bag together to a tube shape with a suitably small diameter which allows easy introduction through a mounting hole in the ventilation container.

By adapting the helical pitch of the elastic thread and the degree of the stretching of the thread during winding, the folded-together diameter of the sheet bag, the resistance of the means against inflation and the self-contractible characteristic may be adapted expediently, so that during inflation the net just receives the energy necessary to ensure suitably rapid discharge of the inflation air and suction of a corresponding amount of fresh air and oxygen into the surrounding ventilation air container.

What is claimed is:

1. A device for performing artificial respiration on a patient which comprises:
   a container having a wall which defines first, second and third openings,
   a first valve device connected to said first opening for enabling gaseous medium to flow into said container and prevent flow of gaseous medium out of said container,
   a second valve device connected to said second opening for enabling gaseous medium to flow out of said container and prevent flow of gaseous medium into said container, and
   an expandable device within said container and connected to said third opening so as to expand when filled with gaseous medium flowing therein through said third opening, thereby forcing gaseous medium in an inner space between said expandable device and said wall of said container through said second opening and said second valve.

2. A device according to claim 1, wherein the container wall that delimits said inner volume is flexible.

3. A device for performing artificial respiration on a patient which comprises:
   a container having a wall which defines first, second and third openings,
   a first valve device connected to said first opening for enabling gaseous medium to flow into said container and prevent flow of gaseous medium out of said container,
   a second valve device connected to said second opening for enabling gaseous medium to flow out of said container and prevent flow of gaseous medium into said container,
   an expansible means within said container which can expand when filled with gaseous medium flowing therein through said third opening, thereby forcing gaseous medium in an inner space between said expansible means and said wall of said container through said second opening and said second valve, and
   means for connecting said expansible means to said third opening.

4. A device according to claim 3, wherein the expansible means is a self-contractible means.

5. A device according to claim 4, wherein the expansible means comprises a bag of a flexible sheet material and an elastic net arranged on the outer side thereof, a bag of an elastic rubber material or a bag of a flexible material formed with corrugations or folds which, when relieved, contract the bag.

6. A device according to claim 4, wherein the expansible means comprises a connecting element adapted to cooperate with a complementary connecting element arranged in said third opening in the container.

7. A device according to claim 6, wherein the complementary connecting elements comprise a bayonet socket, a threaded connection, a conical frictional connection, or a press fit, whereby said expansible means is releasably secured to said third opening.

8. A device according to claim 7, wherein the expansible means is insertable into said container through said third opening.

9. A device according to claim 3, wherein the expansible means comprises a mouthpiece.

* * * * *